US009226866B2

(12) United States Patent
Haseley

(10) Patent No.: US 9,226,866 B2
(45) Date of Patent: Jan. 5, 2016

(54) SPEECH THERAPY DEVICE

(71) Applicant: Susan Ann Haseley, Findlay, OH (US)

(72) Inventor: Susan Ann Haseley, Findlay, OH (US)

( * ) Notice: Subject to any disclaimer, the term of this patent is extended or adjusted under 35 U.S.C. 154(b) by 349 days.

(21) Appl. No.: 13/803,420

(22) Filed: Mar. 14, 2013

(65) Prior Publication Data

US 2014/0100495 A1 Apr. 10, 2014

Related U.S. Application Data

(60) Provisional application No. 61/711,763, filed on Oct. 10, 2012.

(51) Int. Cl.

*A61F 5/58* (2006.01)
*A61H 1/00* (2006.01)
*A61H 21/00* (2006.01)
*A63B 21/04* (2006.01)
*A63B 21/055* (2006.01)
*A63B 23/03* (2006.01)

(52) U.S. Cl.

CPC ................ *A61H 1/008* (2013.01); *A61H 21/00* (2013.01); *A63B 21/0414* (2013.01); *A63B 21/0552* (2013.01); *A63B 23/032* (2013.01); *A61H 2201/168* (2013.01); *A61H 2205/026* (2013.01)

(58) Field of Classification Search

CPC ............ A61H 1/008; A61H 2205/026; A61H 2201/168; A61H 21/00
USPC ........................ 600/23; 128/897–899; 601/23
See application file for complete search history.

(56) References Cited

U.S. PATENT DOCUMENTS 2,748,480 A 6/1956 Weissman
2,818,065 A * 12/1957 Freed .............................. 600/24
3,259,129 A 7/1966 Tepper
3,277,892 A 10/1966 Tepper
3,304,423 A * 2/1967 Medwedeff ................... 378/170
3,462,837 A 8/1969 Andrews et al.
3,556,093 A 1/1971 Quick
3,867,770 A 2/1975 Davis
4,671,766 A * 6/1987 Norton .............................. 433/6
4,718,662 A * 1/1988 North ................... A63B 23/032 128/860
4,723,910 A * 2/1988 Keller ............................... 433/7
4,886,451 A * 12/1989 Cetlin ............................... 433/7
5,169,316 A 12/1992 Lorman et al.
5,257,930 A 11/1993 Blakeley
5,401,234 A * 3/1995 Libin .............................. 600/24
5,718,575 A * 2/1998 Cross, III ............. A63B 71/085 433/6
5,879,155 A * 3/1999 Kittelsen ........................... 433/6
6,446,631 B1 * 9/2002 Hagiwara ............. A61H 39/04 128/848
6,632,095 B2 10/2003 Ryan
6,761,699 B2 7/2004 Chahine
6,971,993 B2 12/2005 Fletcher (Continued)

FOREIGN PATENT DOCUMENTS

WO 2013036737 A1 3/2013

*Primary Examiner* — Navin Natnithithadha
*Assistant Examiner* — Sunita Reddy
(74) *Attorney, Agent, or Firm* — Fraser Clemens Martin & Miller LLC; James D. Miller

(57) ABSTRACT

A speech therapy device configured to be placed in a mouth of a speaker. The speech therapy device includes a first bite plate and a second bite plate disposed opposite the first bite plate. The speech therapy device further includes at least one connecting member disposed between the first bite plate and the second bite plate. A method for using the speech therapy device is also provided.

18 Claims, 4 Drawing Sheets

(56) References Cited

U.S. PATENT DOCUMENTS

| | | | | |
|---|---|---|---|---|
| 7,214,064 | B1 | 5/2007 | Hall | |
| 7,871,199 | B2 * | 1/2011 | Szommer | 378/170 |
| 8,453,650 | B1 * | 6/2013 | Frey | A61C 5/14 128/848 |
| 8,689,796 | B2 * | 4/2014 | Polk, III | 128/861 |
| 2009/0262902 | A1 * | 10/2009 | Gestetner | 378/205 |
| 2009/0308403 | A1 * | 12/2009 | Roettger | A63B 71/085 128/861 |
| 2010/0015565 | A1 * | 1/2010 | Carrillo Gonzalez et al. | 433/7 |
| 2012/0085354 | A1 * | 4/2012 | Polk, III | 128/861 |
| 2012/0109051 | A1 * | 5/2012 | Harrell | A61M 31/002 604/77 |
| 2013/0146066 | A1 * | 6/2013 | Croll | 128/861 |

* cited by examiner

SPEECH THERAPY DEVICE

CROSS-REFERENCE TO RELATED APPLICATION

This application claims priority to U.S. Provisional Patent Application Ser. No. 61/711,763, filed Oct. 10, 2012, the entire disclosure of which is hereby incorporated herein by reference.

FIELD OF THE INVENTION

The invention relates to a speech therapy device, and more particularly to a speech therapy device used to assist a user with pronouncing the /r/ phoneme.

BACKGROUND OF THE INVENTION

Speech is the vocalized form of human communication. Spoken words are created out of the phonetic combination of a limited set of vowels and consonants. Millions of children and adults worldwide are affected by language disorders such as speech sound disorders or articulation disorders, for example. Articulation disorders are based on a difficulty in learning to physically produce the intended phonemes, or a difficulty making sounds. For instance, a child or adult suffering from an articulation disorder may make a /w/ sound when an /r/sound is intended.

Often, articulation disorders are a result of incorrect placement and/or tension of the tongue in a mouth of a speaker. The speaker may find it difficult to visualize the correct location of the tongue and, as a result, speech therapy devices may be particularly helpful to orient the tongue of the speaker properly within the mouth of the speaker.

Speech-Language Pathologists specialize in helping speakers overcome language disorders such as articulation and speech sound disorders. Various treatments aimed at optimizing articulation of individual sounds or minimizing errors in the production of sound patterns are often used by Speech-Language Pathologists. For example, Speech-Language Pathologists may demonstrate to speakers how to produce a sound correctly, teach speakers to recognize which sounds are correct and incorrect, and/or have speakers use various speech therapy devices to practice producing sounds in different words.

Speech therapy devices may be used to help in the pronunciation of certain vowels and/or consonants. Typically, a speech therapy device is positioned in the mouth of the speaker and the speaker practices pronouncing the sound or words containing the sound that is the subject of the articulation disorder of the speaker. As non-limiting examples, U.S. Pat. Nos. 3,867,770, 5,169,316, and 5,257,930 show common elements and features of the prior art. The entire disclosure of each of the above-mentioned patents is hereby incorporated herein by reference. Speech therapy devices currently available, however, are often expensive. Additionally, speech therapy devices are often difficult to use, time consuming, and ineffective.

It would be desirable to have a simple, efficient, cost effective speech therapy device to be used by children and adults suffering from a language disorder, specifically, an inability to correctly pronounce the /r/ sound.

SUMMARY OF THE INVENTION

Consonant with the present invention, a simple, efficient, cost effective speech therapy device to be used by children and adults suffering from a language disorder, specifically, an inability to correctly pronounce the /r/ sound, has surprisingly been discovered.

In one embodiment of the disclosure, a speech therapy device includes a first bite plate, a second bite plate disposed opposite the first bite plate, and at least one connecting member disposed between the first bite plate and the second bite plate. The speech therapy device is configured to be disposed in a mouth of a speaker.

In another embodiment of the disclosure, a speech therapy device includes a substantially t-shaped first bite plate including a first vertically oriented lateral wing and a first plate extending laterally outwardly from an intermediate portion of the first lateral wing and a substantially t-shaped second bite plate disposed opposite the first bite plate including a second vertically oriented lateral wing and a second plate extending laterally outwardly from an intermediate portion of the second lateral wing. The speech therapy device also includes at least one connecting member disposed between the first bite plate and the second bite plate. The at least one connecting member is formed from one of a latex plastic and a non-latex plastic. The speech therapy device is configured to be disposed in a mouth of a speaker.

In another embodiment of the disclosure, a method for using a speech therapy device comprises the steps of providing the speech therapy device including a first bite plate, a second bite plate disposed opposite the first bite plate, and at least one connecting member disposed between the first bite plate and the second bite plate, placing the speech therapy device in a mouth of a speaker, positioning a tongue in the mouth of the speaker under the at least one connecting member and using the tongue to direct the at least one connecting member toward a posterior end of the mouth of the speaker, removing the speech therapy device from the mouth of the speaker; and directing the speaker to pronounce a set of predetermined phonemes and words.

BRIEF DESCRIPTION OF THE DRAWINGS

The above, as well as other advantages of the present invention, will become readily apparent to those skilled in the art from the following detailed description when considered in the light of the accompanying drawing, in which.

DETAILED DESCRIPTION OF AN EMBODIMENT OF THE INVENTION

The following detailed description and appended drawings describe and illustrate an exemplary embodiment of the invention. The description and drawings serve to enable one skilled in the art to make and use the invention, and are not intended to limit the scope of the invention in any manner.

FIGS. 1-6 illustrate a speech therapy device 10 according to an embodiment of the invention. The device 10 includes a first bite plate 12, a second bite plate 14, and at least one connecting member 16. The device 10 is configured to be positioned in a mouth of a speaker in order to aid the speaker in pronouncing different phonemes such as the /r/phoneme, for example.

Figure 1:
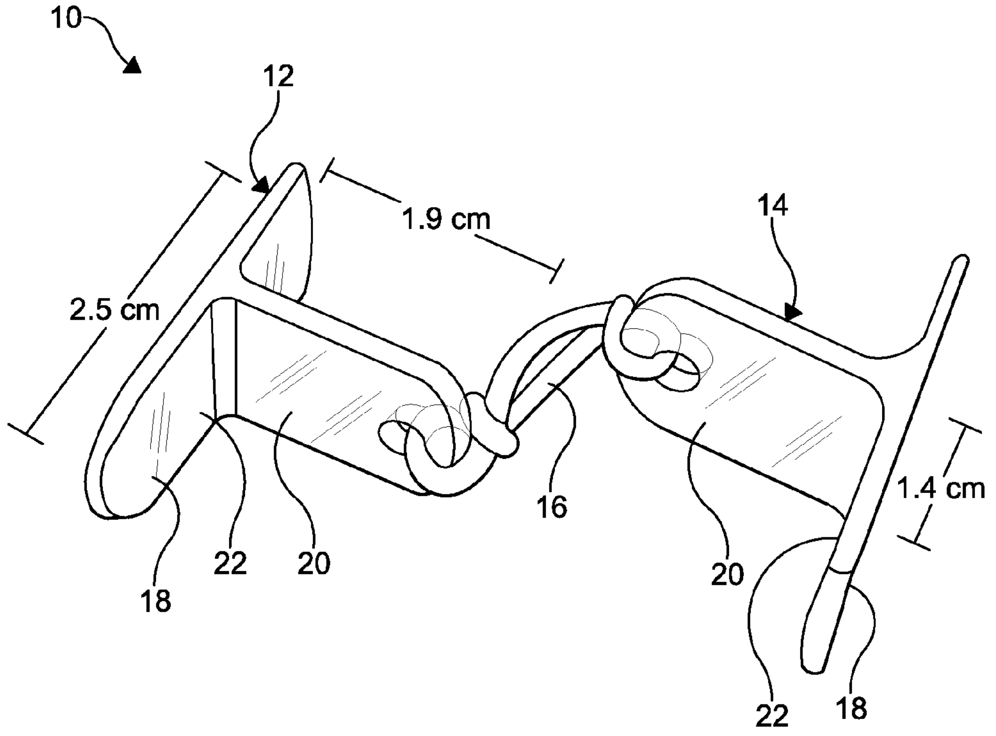
FIG. 1 is a side perspective view of a speech therapy device according to one embodiment of the invention.
Figure 2:
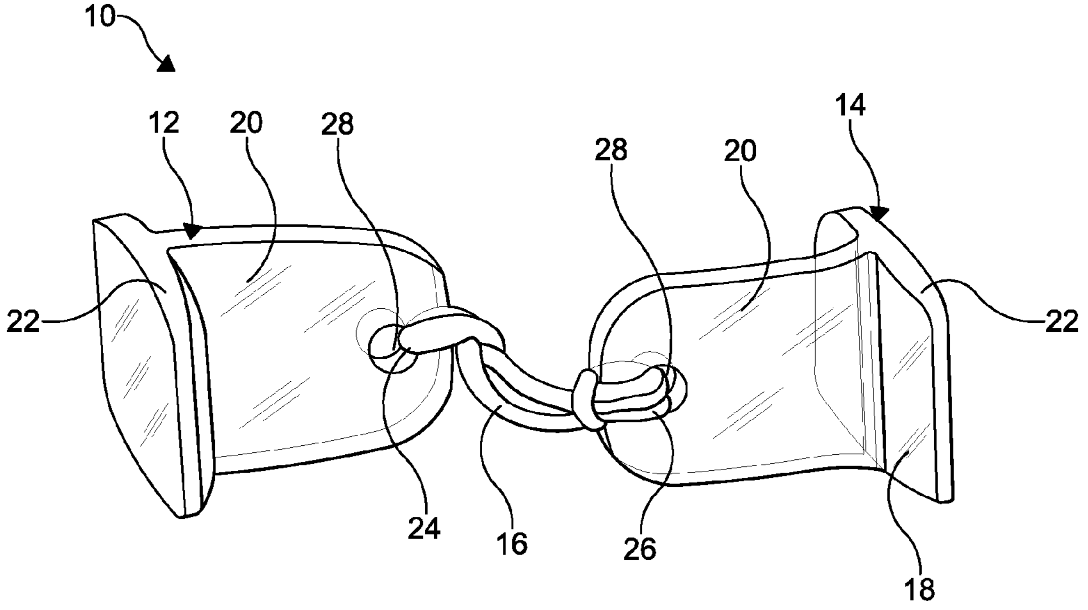
FIG. 2 is a top perspective view of the speech therapy device shown in FIG. 1.
Figure 3:
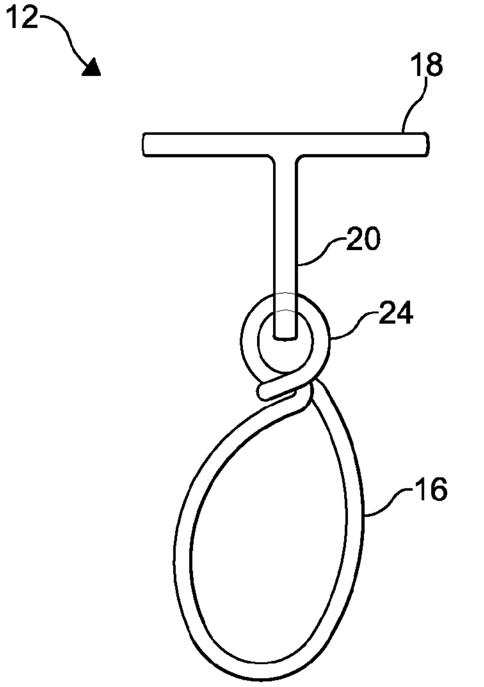
FIG. 3 is a side plan view of a bite plate and a connecting member of the speech therapy device shown in FIGS. 1 and 2.
Figure 4:
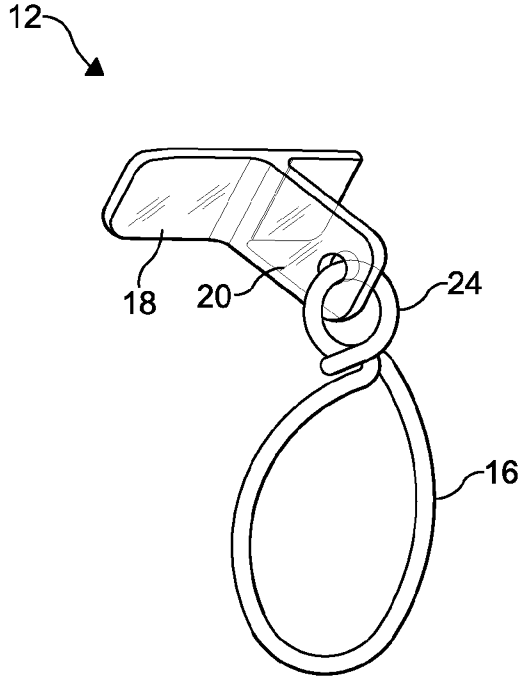
FIG. 4 is a perspective view of the bite plate and the connecting member of the speech therapy device shown in FIGS. 1, 2, and 3.
Figure 5:
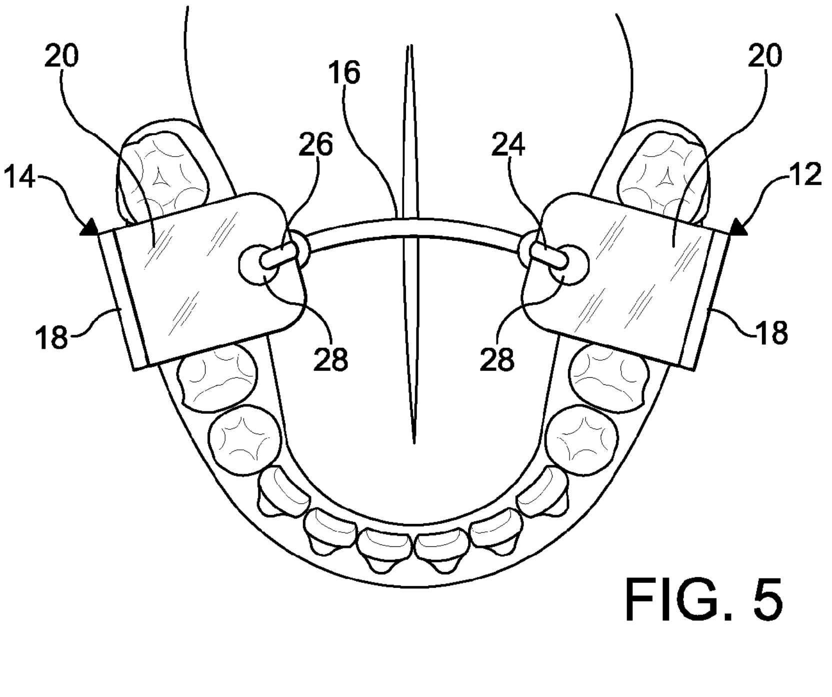
FIG. 5 is a top elevational view of speech therapy device shown in FIG. 1 positioned in a mouth of a user.
Figure 6:
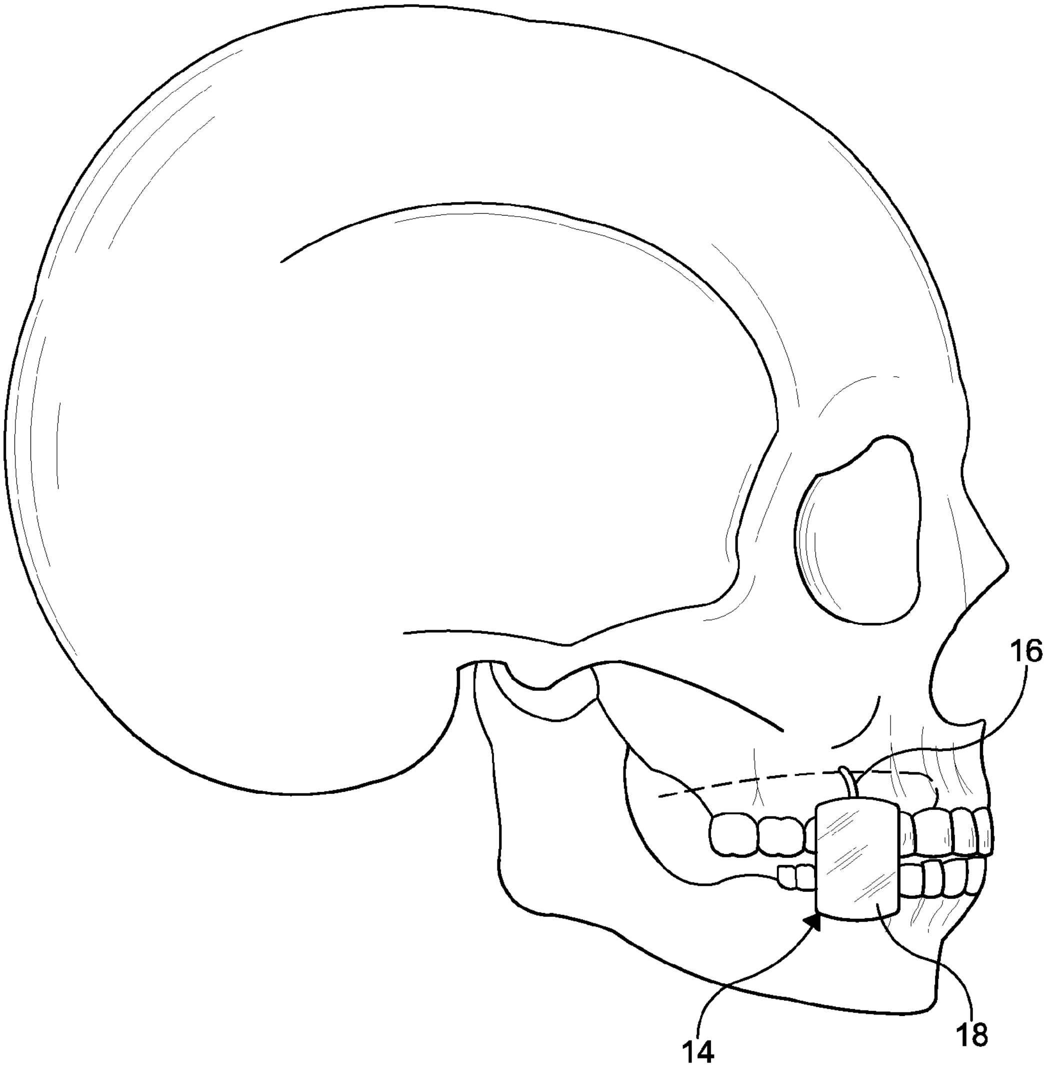
FIG. 6 is a side cross-sectional perspective view of the speech therapy device shown in FIG. 1 positioned in a mouth of a user.

The first bite plate 12 is typically produced from an orthodontic resin, but may be produced from any non-toxic, substantially non-pliable, smooth material for inserting into the mouth of the speaker such as BPA free plastic, for example. The orthodontic resin may be produced from a combination of resin and powder in certain embodiments. For example, an acrylic liquid monomer and a powder polymer may be used. The resin and powder may be mixed in a ratio of 1-1 parts. The mixture of resin and powder is then poured into flexible molds. Once the first bite plate 12 is removed from the mold, a tool may be used to add texture to or smooth an exterior surface of the first bite plate 12. Alternatively, the first bite plate 12 may be formed by injection molding or any other appropriate means. As shown in FIGS. 1, 2, and 4, the first bite plate 12 may be translucent. The first bite plate 12 may also be opaque, if desired.

The first bite plate 12 is substantially t-shaped with a lateral wing 18 configured to be positioned substantially vertically in the mouth of the speaker and a plate 20 extending laterally outwardly from an intermediate portion 22 of the lateral wing 18. Accordingly, in certain embodiments the lateral wing 18 and the plate 20 are substantially perpendicular to one another. A shape of the lateral wing 18 and a shape of the plate 20 are typically rectangular but may be any shape such as circular, semi-circular, oval, or asymmetrical, for example.

As illustrated in FIG. 1, in certain embodiments of the disclosure, the lateral wing is about 2.5 centimeters long and about 1.4 centimeters wide, and the plate 20 is about 1.9 centimeters long and 1.4 centimeters wide. However, the first bite plate 12 may be any shape and size capable of being inserted into the mouth of the speaker so that the plate 20 is secured between a top row of teeth and a bottom row of teeth on a first side in the mouth of the speaker. A thickness of the lateral wing 18 and the plate 20 may vary as desired to permit the device 10 to comfortably rest in the mouth of the speaker when the device 10 is in use. Typically, the plate 20 of the first bite plate 12 is secured between an upper second bicuspid and a lower second bicuspid on the first side in the mouth of the speaker. An inner surface of the lateral wing 18 is disposed adjacent an outer surface of the upper second bicuspid and the lower second bicuspid on the first side of the mouth of the speaker. Alternatively, the first bite plate 12 may be secured between an upper first bicuspid and a lower first bicuspid, or the first bite plate 12 may be positioned elsewhere in the mouth of the speaker based on a size and shape of the mouth of the speaker, a preference of the speaker, and/or a preference of the Speech-Language Pathologist.

The second bite plate 14 is substantially identical to the first bite plate 12 and typically produced from an orthodontic resin, but may also be produced from any non-toxic, substantially pliable, smooth material for inserting into the mouth of the speaker. As shown in FIGS. 1, 2, and 4, the second bite plate 14 may be translucent. The second bite plate 14 may also be opaque, if desired.

The second bite plate 14 is substantially t-shaped with a lateral wing 18 configured to be positioned substantially vertically in the mouth of the speaker and a plate 20 extending laterally outwardly from an intermediate portion 22 of the lateral wing 18. Accordingly, in certain embodiments, the lateral wing 18 and the plate 20 are substantially perpendicular to one another. A shape of the lateral wing 18 and a shape of the plate 20 are typically rectangular but may be any shape such as circular, semi-circular, oval, or asymmetrical, for example. However, the second bite plate 14 may be any shape and size capable of being inserted into the mouth of the speaker with the plate 20 secured between the top row of teeth and the bottom row of teeth on a second side of the mouth of the speaker. Typically, the size, shape, and thickness of the first bite plate 12 and the second bite plate 14 are substantially the same. However, in certain embodiments the size, shape, and thickness of the first bite plate 12 and the second bite plate 14 may be different. The second bite plate 14 is typically secured between an upper second bicuspid and a lower second bicuspid on the second side in the mouth of the speaker. Alternatively, the second bite plate 14 may be secured between an upper first bicuspid and a lower second bicuspid, or the second bite plate 14 may be positioned elsewhere in the mouth of the speaker based on the size and shape of the mouth of the speaker, the preference of the speaker, and/or the preference of the Speech-Language Pathologist.

The at least one connecting member 16 is typically produced from a non-toxic, resilient material capable of expanding and contracting in the mouth of the speaker. Materials such as latex plastic and non-latex plastic, for example, may be used for the at least one connecting member 16. In certain embodiments, one or more orthodontic elastic bands looped together or otherwise connected may be used to connect the first bite plate 12 and the second bite plate 14.

The at least one connecting member 16 may be any length and thickness capable of providing tension when a tongue of the speaker presses against the connecting member 16. A first end 24 of the at least one connecting member 16 is connected to the first bite plate 12 and a second end 26 of the at least one connecting member 16 is connected to the second bite plate 14. As illustrated in FIGS. 1-4, typically, the first end 24 and the second end 26 of the at least one connecting member 16 are inserted through an aperture 28 formed in the first bite plate 12 and the second bite plate 14, respectively. The first end 24 and the second end 26 of the at least one connecting member 16 may connect to the first bite plate 12 and the second bite plate 14 using any connecting means such as a tie or a loop, for example, or may be formed integrally with the first bite plate 12 and the second bite plate 14. The at least one connecting member 16 may be interchangeable with additional connecting members 16 and/or adjustable in length in order to accommodate various mouths having different shapes and sizes.

Figure 7:
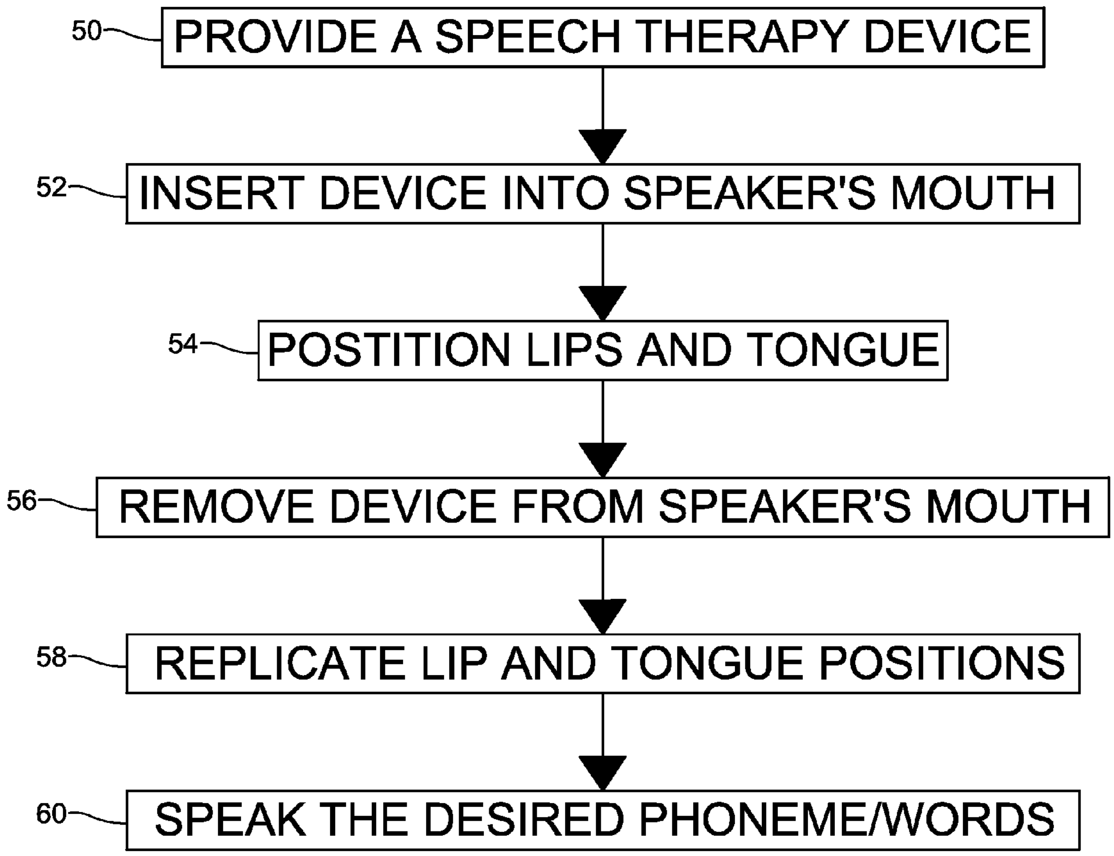
FIG. 7 illustrates the steps of a method for using the speech therapy device according to the invention.

In one embodiment of the disclosure, illustrated in FIG. 7, a method for using a speech therapy device includes the following steps. The speaker typically has a speech sound disorder such as an articulation disorder. For illustrative purposes, the speaker may have a difficult time producing the /r/ phoneme, for example. In a first step 50, a speech therapy device 10 is provided to the speaker. In step 52, the device 10 is inserted into the mouth of the speaker. The first bite plate 12 is positioned on the first side of the mouth of the speaker and the second bite plate 14 is positioned on the second side of the mouth of the speaker. The speaker is instructed to bite down on the plate 20 of the first bite plate 12 and the plate 20 of the second bite plate 14. The speech therapy device 10 is positioned correctly, for example, when the plate 20 of the first bite plate 12 is disposed between the upper second bicuspid and the lower second bicuspid on the first side of the mouth of the speaker, and the plate 20 of the second bite plate 14 is disposed between the upper second bicuspid and the lower second bicuspid on the second side of the mouth of the speaker. The speaker is able to stabilize the device 10 by biting down on the plates 20 and the tongue is free to move into a proper position within the mouth in order to produce the /r/ phoneme.

Next, in step 54, the speaker is directed to expose the top row of teeth and the bottom row of teeth by extending outwardly an upper lip and a lower lip of the speaker and making a "shhh" sound. The speaker is then directed to position a top surface of the tongue under the at least one connecting member 16 and to use the tongue to direct the at least one connecting member 16 toward the posterior end of the mouth. The speaker may be directed to produce the /r/ phoneme while in the above position if desired. Typically, the device 10 is disposed in the mouth of the speaker for about 30 seconds, but the period of time the device 10 remains in the mouth of the speaker may vary.

In step 56, the device 10 is then removed from the mouth of the speaker and in step 58, the speaker is directed to replicate the position that the upper lip, the lower lip, and the tongue were in before removing the device 10. Finally, in step 60, the speaker is then directed to speak the /r/ phoneme and/or words that include the /r/phoneme to practice without the device 10. It may be necessary for the speaker to repeat the steps of the above-described method in order to improve articulation of the /r/ phoneme.

The above-described device 10 has several advantages. First, the device is easy and inexpensive to produce. Accordingly, it is affordable for institutions such as schools to purchase, for example. Additionally, the device 10 is easy to use for both the Speech-Language Pathologists and the speakers. Furthermore, the device 10 allows a speaker to improve articulation of desired phonemes quickly and confidently.

From the foregoing description, one ordinarily skilled in the art can easily ascertain the essential characteristics of this invention and, without departing from the spirit and scope thereof, can make various changes and modifications to the invention to adapt it to various usages and conditions.

What is claimed is:

1. A speech therapy device comprising:

a first bite plate configured to be received in a mouth of a speaker between a first upper tooth and a first lower tooth on a first side of the mouth of the speaker;

a second bite plate disposed opposite the first bite plate and configured to be received in the mouth of the speaker between a second upper tooth and a second lower tooth on a second side of the mouth of the speaker; and at least one flexible connecting member extending between the first bite plate and the second bite plate;

wherein the speech therapy device is configured to be stabilized with a jaw of the speaker by fixing the first bite plate between the first upper tooth and the first lower tooth and by fixing the second bite plate between the second upper tooth and the second lower tooth; and wherein the at least one connecting member is configured to arrange a tongue of the speaker into a predetermined location, placement and tension within the mouth of the speaker, and wherein the at least one connecting member is configured to be directed toward a posterior of the mouth of the speaker with the tongue of the speaker, aiding the speaker with /r/ phoneme pronunciation.

2. The speech therapy device of claim 1, wherein the first bite plate is substantially t-shaped and includes a first vertically oriented lateral wing and a first plate extending laterally outwardly from an intermediate portion of the first lateral wing, and wherein the second bite plate is substantially t-shaped and includes a second vertically oriented lateral wing and a second plate extending laterally outwardly from an intermediate portion of the second lateral wing.

3. The speech therapy device of claim 2, wherein the first lateral wing, the first plate, the second lateral wing, and the second plate have a substantially rectangular shape.

4. The speech therapy device of claim 1, wherein the first bite plate and the second bite plate are formed from at least one of an orthodontic resin and plastic.

5. The speech therapy device of claim 1, wherein the at least one connecting member is formed by at least one of a latex plastic and a non-latex plastic.

6. The speech therapy device of claim 1, wherein the at least one connecting member is formed by one or more orthodontic elastic bands.

7. The speech therapy device of claim 1, wherein the first bite plate has a first aperture through which a first end of the at least one connecting member is disposed and the second bite plate has a second aperture through which a second end of the at least one connecting member is disposed.

8. The speech therapy device of claim 1, wherein the first bite plate is disposed between an upper second bicuspid and a lower second bicuspid on a first side of the mouth of the speaker, and the second bite plate is disposed between an upper second bicuspid and a lower second bicuspid on a second side of the mouth of the speaker.

9. A speech therapy device comprising:

a substantially t-shaped first bite plate configured to be received in a mouth of a speaker between a first upper tooth and a first lower tooth on a first side of the mouth of the speaker including a first vertically oriented lateral wing and a first plate extending laterally outwardly from an intermediate portion of the first lateral wing;

a substantially t-shaped second bite plate disposed opposite the first bite plate and configured to be received in the mouth of the speaker between a second upper tooth and a second lower tooth on a second side of the mouth of the speaker including a second vertically oriented lateral wing and a second plate extending laterally outwardly from an intermediate portion of the second lateral wing; and at least one flexible connecting member extending between the first bite plate and the second bite plate, the at least one connecting member formed by at least one of a latex plastic and a non-latex plastic;

wherein said speech therapy device is configured to be stabilized with a jaw of the speaker by fixing the first bite plate between the first upper tooth and the first lower tooth and by fixing the second bite plate between the second upper tooth and the second lower tooth; and wherein the at least one connecting member is configured to arrange a tongue of the speaker into a predetermined location, placement and tension within the mouth of the speaker, and wherein the at least one connecting member is configured to be directed toward a posterior of the mouth of the speaker with the tongue of the speaker, aiding the speaker with /r/ phoneme pronunciation.

10. The speech therapy device of claim 9, wherein the first bite plate and the second bite plate are foamed from at least one of an orthodontic resin and plastic.

11. The speech therapy device of claim 9, wherein the at least one connecting member is formed by one or more orthodontic bands.

12. The speech therapy device of claim 9, wherein the first bite plate has a first aperture through which a first end of the at least one connecting member is disposed and the second bite plate has a second aperture through which a second end of the at least one connecting member is disposed.

13. A method for using a speech therapy device comprising the steps of:

providing the speech therapy device including a first bite plate, a second bite plate disposed opposite the first bite plate, and at least one flexible connecting member disposed between the first bite plate and the second bite plate;

placing the speech therapy device into a mouth of a speaker with the first bite plate configured to be received into the mouth of the speaker between a first upper tooth and a first lower tooth on a first side of the mouth of the speaker; the second bite plate disposed opposite the first bite plate and configured to be received in the mouth of the speaker between a second upper tooth and a second lower tooth on a second side of the mouth of the speaker; the at least one flexible connecting member extending between the first bite plate and the second bite plate; wherein by fixing the first bite plate between the first upper tooth and the first lower tooth and by fixing the second bite plate between the second upper tooth and the second lower tooth, the speech therapy device is configured to be stabilized with a jaw of the speaker;

directing the speaker to locate, place and tense a tongue in the mouth of the speaker under the at least one connecting member and use the tongue to direct the at least one connecting member toward a posterior end of the mouth of the speaker;

maintaining the location, placement and tension of the tongue in the mouth of the speaker for a therapeutically effective predetermined interval;

removing the speech therapy device from the mouth of the speaker; and directing the speaker to pronounce /r/ phoneme and a set of /r/ phonemes comprising words.

14. The method of claim 13, wherein the first bite plate and the second bite plate are formed from at least one of an orthodontic resin and plastic.

15. The method of claim 13, wherein the at least one connecting member is formed by at least one of a latex plastic and a non-latex plastic.

16. The method of claim 13, wherein during the maintaining step the speaker is directed to pronounce /r/ phoneme and a set of /r/ phoneme comprising words before the step of removing the speech therapy device from the mouth of the speaker.

17. The method of claim 13, wherein the predetermined interval is about 30 seconds.

18. The method of claim 13, wherein the steps including placing the speech therapy device in a mouth of a speaker, directing the speaker to locate, place and tension a tongue in the mouth of the speaker under the at least one connecting member and use the tongue to direct the at least one connecting member toward a posterior end of the mouth of the speaker, removing the speech therapy device from the mouth of the speaker, and directing the speaker to pronounce /r/ phoneme and a set of /r/ phoneme comprising words are repeated at least once.

* * * * *